United States Patent
Nienaber et al.

(12) 
(10) Patent No.: US 6,690,763 B2
(45) Date of Patent: Feb. 10, 2004

(54) DEVICE FOR MICRO-MANIPULATION OF SMALL SAMPLES

(75) Inventors: Terrence J. Nienaber, Pearland, TX (US); William C. Robertson, Houston, TX (US); Kent D. Copeland, Houston, TX (US)

(73) Assignee: Oceaneering International, Inc., Houston, TX (US)

( * ) Notice: Subject to any disclaimer, the term of this patent is extended or adjusted under 35 U.S.C. 154(b) by 297 days.

(21) Appl. No.: 09/899,668

(22) Filed: Jul. 5, 2001

(65) Prior Publication Data

US 2002/0159560 A1 Oct. 31, 2002

Related U.S. Application Data

(60) Provisional application No. 60/287,247, filed on Apr. 28, 2001.

(51) Int. Cl.[7] .............................................. G01N 23/20
(52) U.S. Cl. ........................................... 378/81; 378/79
(58) Field of Search ............................. 378/81, 79, 71, 378/80, 86, 208

(56) References Cited

U.S. PATENT DOCUMENTS

| | | | | |
|---|---|---|---|---|
| 3,600,576 A | * | 8/1971 | Carter et al. | 378/81 |
| 4,058,731 A | | 11/1977 | Muller et al. | |
| 4,641,329 A | | 2/1987 | Green et al. | |
| 4,710,259 A | | 12/1987 | Howe et al. | |
| 4,766,465 A | * | 8/1988 | Takahashi | 355/53 |
| 5,127,039 A | * | 6/1992 | Hesch | 378/79 |
| 5,769,086 A | * | 6/1998 | Ritchart et al. | 600/566 |
| 6,545,440 B2 | * | 4/2003 | Slater et al. | 318/567 |

\* cited by examiner

*Primary Examiner*—Louis Arana
(74) *Attorney, Agent, or Firm*—Duane Morris LLP

(57) ABSTRACT

The present invention is directed to a x-y-axis device and a x-y-z-axis device for micro-manipulating or positioning a crystal for x-ray diffraction. More specifically, the devices which may be placed on the head on a goniometer have small footprints (small in size). The sample may be moved and recorded in step resolutions of 1 micron over an extended range of motion.

12 Claims, 6 Drawing Sheets

US 6,690,763 B2

DEVICE FOR MICRO-MANIPULATION OF SMALL SAMPLES

RELATED APPLICATIONS

This application is based on Provisional Application No. 60/287,247, filed Apr. 28, 2001, entitled "Device for Micro-Manipulation of Small Samples".

FIELD OF THE INVENTION

The present invention is directed to a device for micro-manipulation of small samples. More specifically, the present invention is to provide x-y movement or x-y-z movement to a sample affixed to a goniometer.

BACKGROUND OF THE INVENTION

U.S. Pat. No. 4,058,731 discloses a corpuscular-beam apparatus including a specimen holder having at least two degrees of freedom of translation and at least one degree of freedom of rotation, and control means for correcting the translational coordinates of the specimen holder automatically when the specimen holder is rotated and retraining a predetermined specimen point in its position in the apparatus.

U.S. Pat. No. 4,641,329 discloses a fixture for supporting and aligning small samples of material on a goinometer for x-ray diffraction.

U.S. Pat. No. 4,710,259 discloses a method and apparatus for x-raying a crystal.

SUMMARY OF THE INVENTION

The present invention is directed to a x-y-axis device and a x-y-z-axis device for micro-manipulating or positioning a crystal for x-ray diffraction. More specifically, the devices which may be placed on the head on a goniometer have small footprints (small in size). The sample may be moved and recorded in step resolutions of 1 micron over an extended range of motion.

DESCRIPTION OF THE PREFERRED EMBODIMENTS

The present invention is illustrated as a device for mounting on a goniometer for studing crystal structure of materials, such as the x-ray of protein crystals to determne structure and chemical characteristics. Goniometers are known in the art and have various configurations. The device of the present invention is mounted to the goniometer to provide precise and measured movement either in the x-y axis or the x-y-z axis of the crystal sample. There may be uses other than crystallography for the present invention to align small samples.

One significant feature of the devices of the present invention is the precise motorized control of the position of the sample, with the device capable of moving the sample in fractional or single micrometer steps for accurate positioning control. The step resolution is currently configured to 1 micron in the x-y stages and 2.4 microns in the z-stage, however the design easily allows resolutions on the order of 0.2 microns. The position of the sample is controlled and tracked via open loop or closed loop feedback, with a home sensor providing a repeatable starting position.

Another feature of the devices of the present invention is the large distances of linear travel available in each axis, on the order of 6 mm (millimeter). To accomplish the linear travel, linear slides of very low friction are used, allowing precise resolution with small amounts of torque and very small motors.

Still another feature of the devices of the present invention is that the size of the device is very small and therefore the shadowing created by the device while x-raying is reduced relative to devices of the prior art. A more precise and nearly unobstructed x-ray diffraction image of the crystal is possible with the devices of the present invention. Because small motors are used, allowing the drive motors to be embedded inside the housing of the device, the overall footprint and height of the devices are smaller than devices of the prior art. In the stated configuration, the x-y-z device is contained within a cylindrical working volume of less than 57 mm (millimeter) diameter by 33 mm high. The x-y device is contained within a rectangular working volume of 47 mm by 47 mm by 16 mm high. Each of these working volumes may be increased to increase the range of travel if needed.

Figure 1:
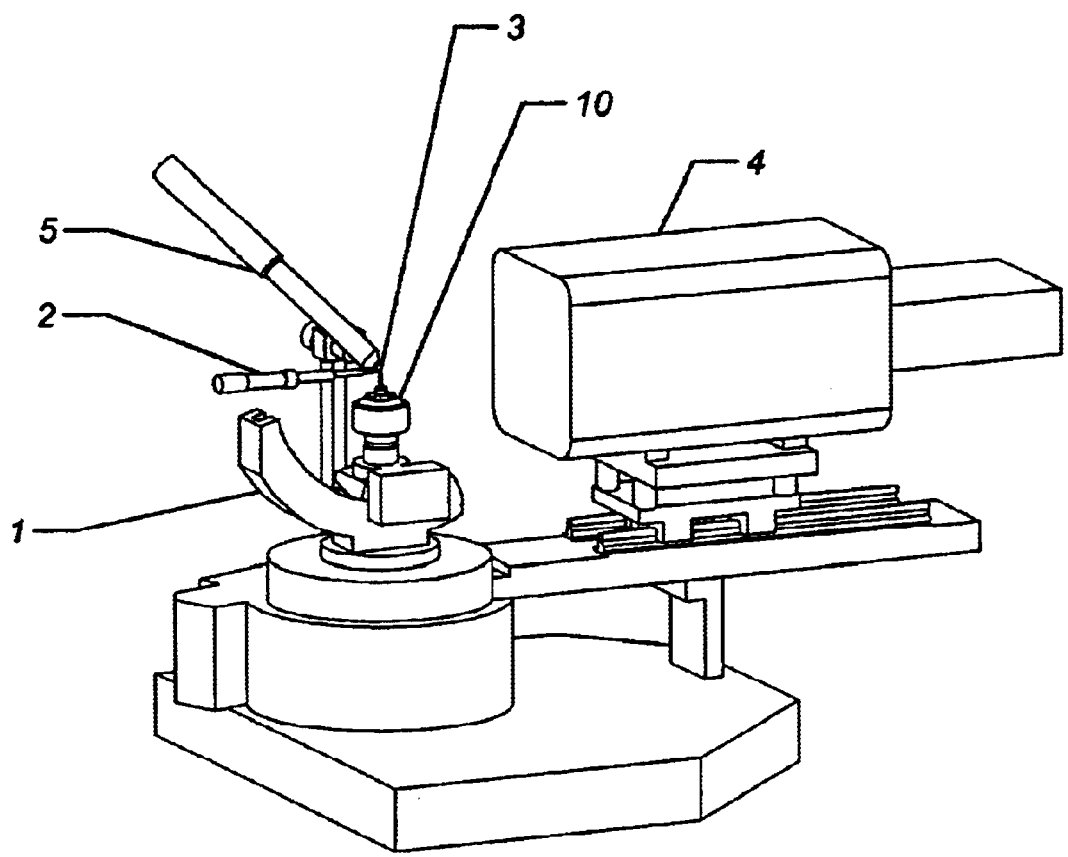
FIG. 1 is a schematic view of a typical installation of a multi-axis positioner with a crystal on a goniometer.

Referring now to FIG. 1, the devices of the present invention are described as a replacement to current manual goniometer heads used in crystallography. The goniometer 1 is a 4-circle goniometer (Ref.: Rigaku/MSC Model: AFC9). An x-ray source 2 is directed at the sample 3. The diffracted rays are captured on the face of x-ray detector 4. When the crystal sample 3 is a protein, for example, a source of nitrogen 5 is required to maintain the crystal as a cryogenically frozen solid. The manual head of goniometer 1 is replaced by the head or device 10 of the present invention. It is understood that the device 10 shown is a x-y-z-axis device; however there are goniometers that have one stage of movement, usually the z-axis, of the sample 3 and in that instance a x-y-axis device 10 replaces the manual head. Goniometer 1 is a device used to control the orientation of the crystal sample during the visual or x-ray diffraction process. The head of goniometer 1 allows the sample to be moved to the center of rotation of the goniometer axes while in the focus of the optical or x-ray line of site. The goniometer head must be small in footprint to allow the maximum possible area of access of x-ray source to the sample from various angles during the movement of the sample to different orientations. Conventional motorized stages do not fit within the allotted height, or have too large a footprint, to be used as a head of a goniometer.

Figure 2:
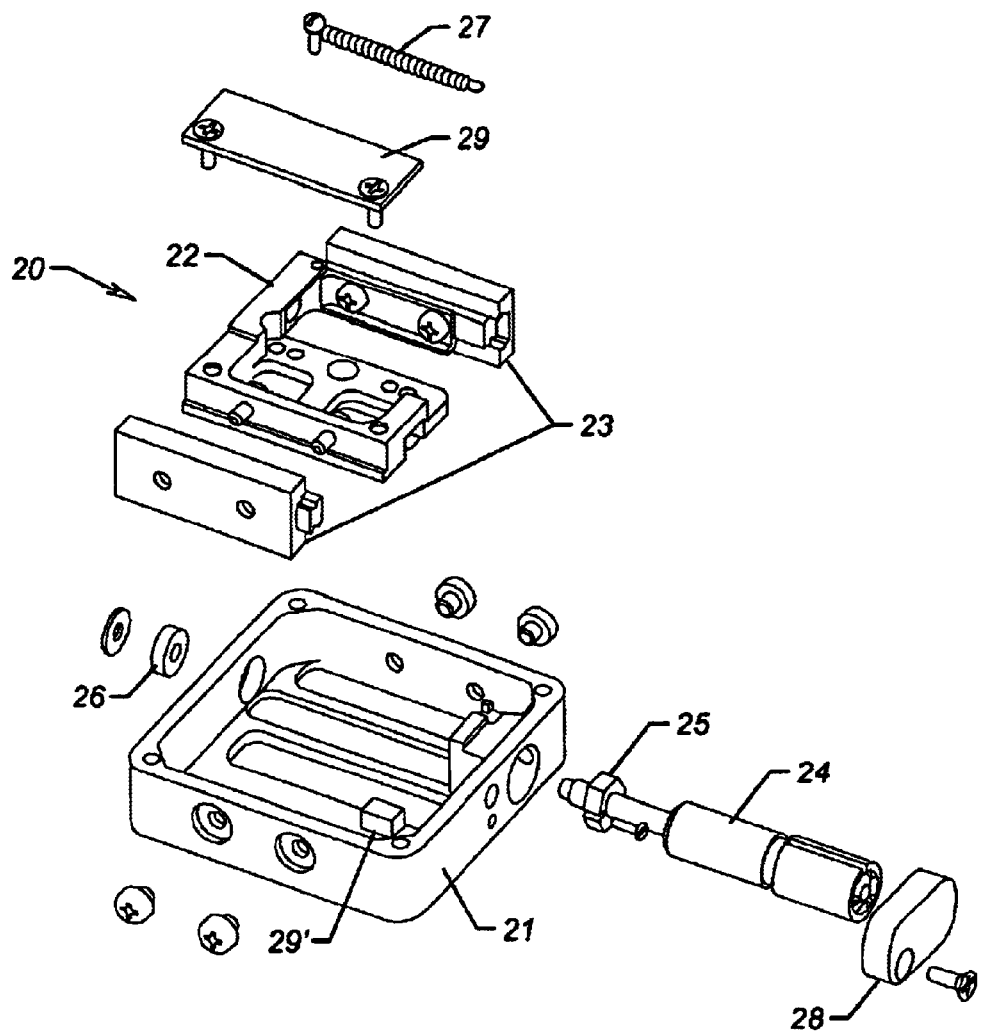
FIG. 2 is an exploded view of a x-stage or y-stage positioner.
Figure 3:
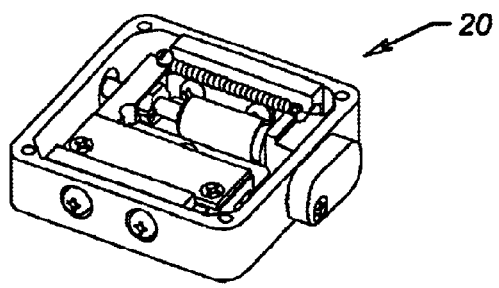
FIG. 3 is an isometric view of an assembled x-stage or y-stage positioner.

Referring now to FIG. 2 and FIG. 3, an exploded view of a y-axis device 20 and an assembled view of y-axis device 20 are shown respectively. Device 20 has a housing 21, preferably made of aluminum to shield the inner pieces from the cold nitrogen stream. A U-shaped carriage 22 is attached to linear ball slides 23, one on each side of the U-shaped carriage 22. The carriage 22 and ball slides 23 are placed inside the housing 21 and a motor 24 having a threaded shaft with a nut 25 on the shaft is inserted into an opening in the housing 21. The end of the threaded shaft is held by a bearing 26 in an opening in the opposite wall of housing 21. The carriage 22 is moved so that the nut 25 is firmly held in the opening in the carriage that the shaft passes through. The linear ball slides 23 are screwed to the housing 21. All parts of the device are finely machined and the assembly aligns and places all parts in operating position. To further reduce play, a spring 27 biases the carriage 22 toward the direction of motor 24. Also, the U-shape configuration of the carriage 22 provides a compliant linkage to provide a light preload that reduces slop in the side-to-side motion between the ball slides. A motor cover 28 is affixed to the outside of housing 21.

An optical sensor 29 is mounted on the carriage 22. Housing 21 having a protrusion 29' provides a centering or zero position for the carriage 22 when the protrusion 29' and the sensor 29 are aligned. The signal from sensor 29 is sent to a computer (not shown) that records and controls the operation of the device 20.

Figure 4:
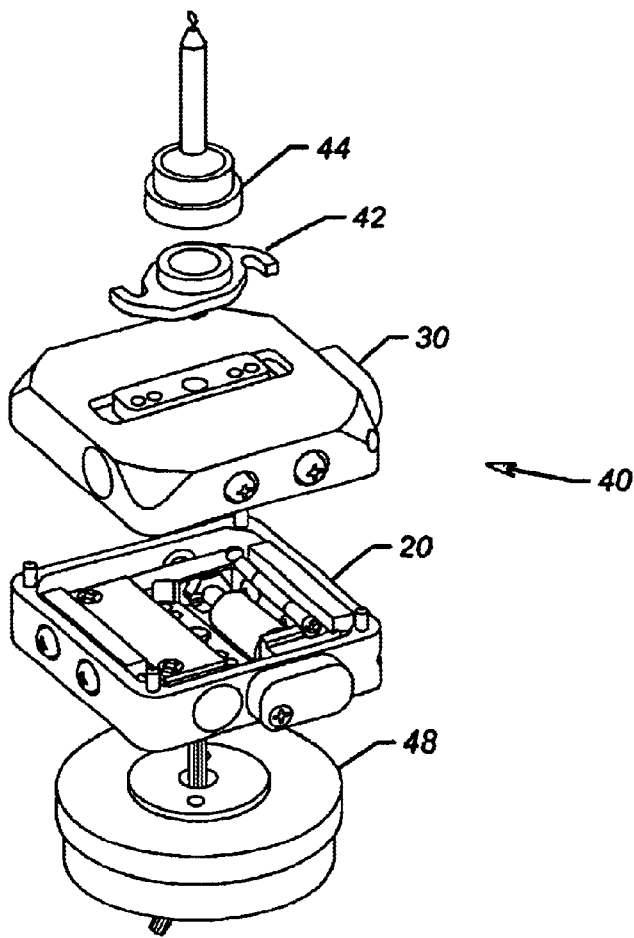
FIG. 4 is an exploded view of a x-y stage micro-manipulator or positioner of the present invention.
Figure 5:
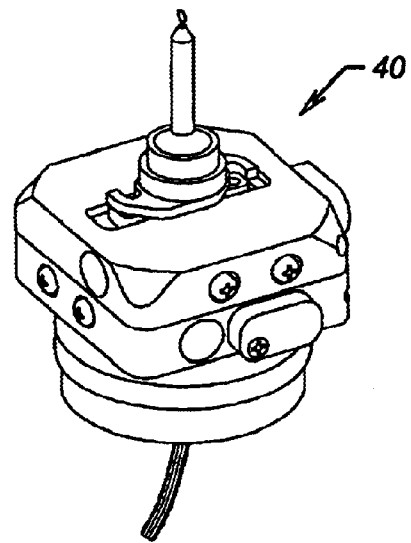
FIG. 5 is an isometric view of an assembled x-y stage micro-manipulator or positioner of the present invention.

Referring now to FIG. 4, a x-y-axis device 40 is shown in an exploded view. The x-y-axis device 40 is comprised of a y-axis device 20, as described above, and a functionally identical x-axis device 30. Housing 21 of x-axis device 30 is mounted on the housing 21 of the y-axis device 20 at a right angle. Orthogonal linear travel is achieved by attaching the carriage 22 of the y-axis device 20 to an adapter 48 which connects the device 20 to the goniometer 1. A magnetic base adapter 42 is mounted on the carriage 22 of the x-axis device 30 which allows for the use of a sample-mounting pin with a ferrous base 44 to be used in conjunction with the x-y-axis device 40. In this manner, the y-axis device 20 moves the mated housings 21 in the y-direction, and the x-axis device 30 moves the magnetic base adapter 42 and sample-mounting pin 44 in the x-direction. The fully assembled x-y-axis device 40 is shown in FIG. 5. It is understood that this device 40 may be used on a goniometer 1 that has a z-axis positioner, which is known in the art.

Figure 6:
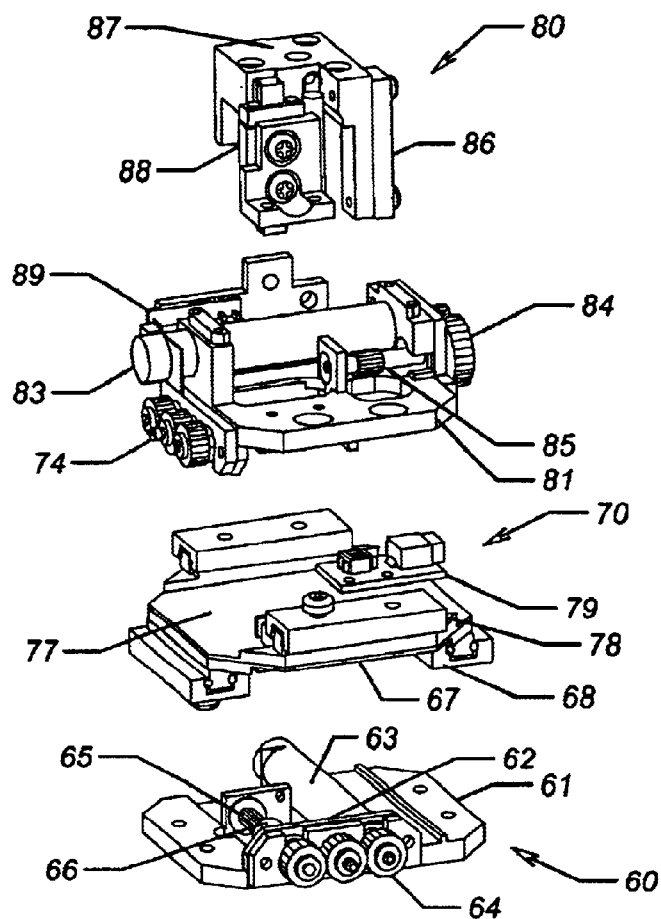
FIG. 6 is an exploded view showing one side of a x-y-z stage positioner.
Figure 8:
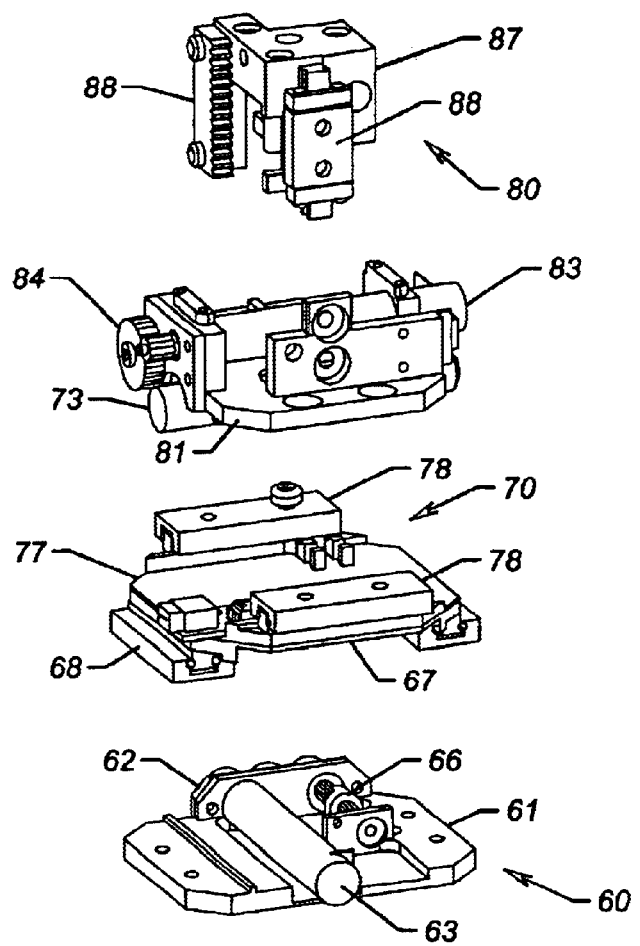
FIG. 8 is an exploded view showing the reverse side of a x-y-z stage positioner shown in FIG. 6.

Referring now to FIG. 6, a x-y-z-axis device 50 is illustrated in an exploded view. In a x-y-z-axis device 50 the y-axis device and the x-axis device may be devices 20 and 30 respectively as described herein above. However, another embodiment of these devices is illustrated. Both FIGS. 6 and 8 may need to be viewed to see all sides of device 50 since FIG. 6 is an isometric view in one direction and FIG. 8 is the isometric view 180□ in the other direction. In this embodiment y-axis device 60 is built on a base 61. The housing in this embodiment has been omitted for clarity, but the housing covers the assembly and again protects the internal workings from particulate contamination and the cold nitrogen stream from nozzle 5. Base 61 has a mounting structure 62 at right angle to the base. The motor 63 drives a series of gears 64 that drive a screw 65. A nut 66 attached to the bottom of a carriage 67 is moved by screw 65 during rotation of the screw by the motor 63. The carriage 67 is mounted on two linear slides 68.

The x-axis device 70 is functionally identical to the y-axis device 60 but turned at right angles. Carriage 77 is either attached directly to carriage 67, or as shown in this embodiment, the two pieces may be constructed as a single item. The x-axis motor 73 drives the gears 74 and moves carriage 77 mounted on two linear slides 78. A home sensor 79 is mounted on the carriage 77 so that when the carriage aligns with the base 81 above, the centering of the carriage can be recorded and the movement controlled.

The z-axis device 80 is mounted by base 81 to the carriage 77 of the x-axis device 70. The z-axis motor 83 drives a gear drive 84 connected to a shaft. On rotation of the z-axis shaft a pinion 85 is rotated that is connected to a rack 86. The carriage 87 moves vertically. The pair of vertically extending linear slides 88 together with the rack 86 maintain the carriage 87 steady in its vertical movement. A home sensor 89 is mounted to the base structure 81 so that when the base 81 aligns with the protrusion on carriage 87, the location of the reference spot may be recorded and the movement controlled.

Figure 7:
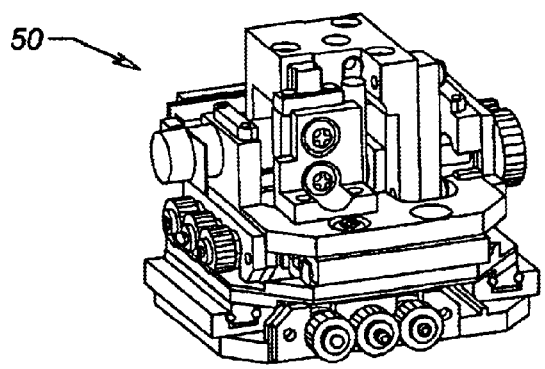
FIG. 7 is an isometric view of the assembled x-y-z stage positioner shown in FIG. 6.
Figure 9:
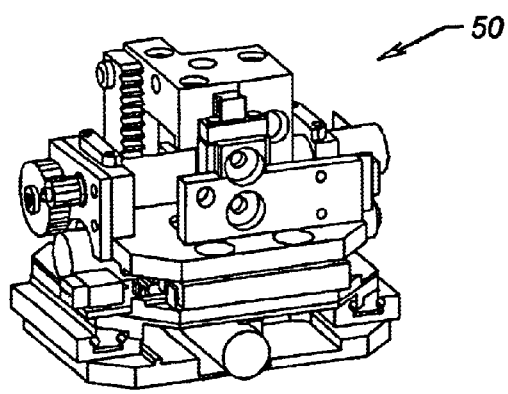
FIG. 9 is an isometric view of the assembled reverse side of the x-y-z stage positioner shown in FIG. 8.
Figure 10:
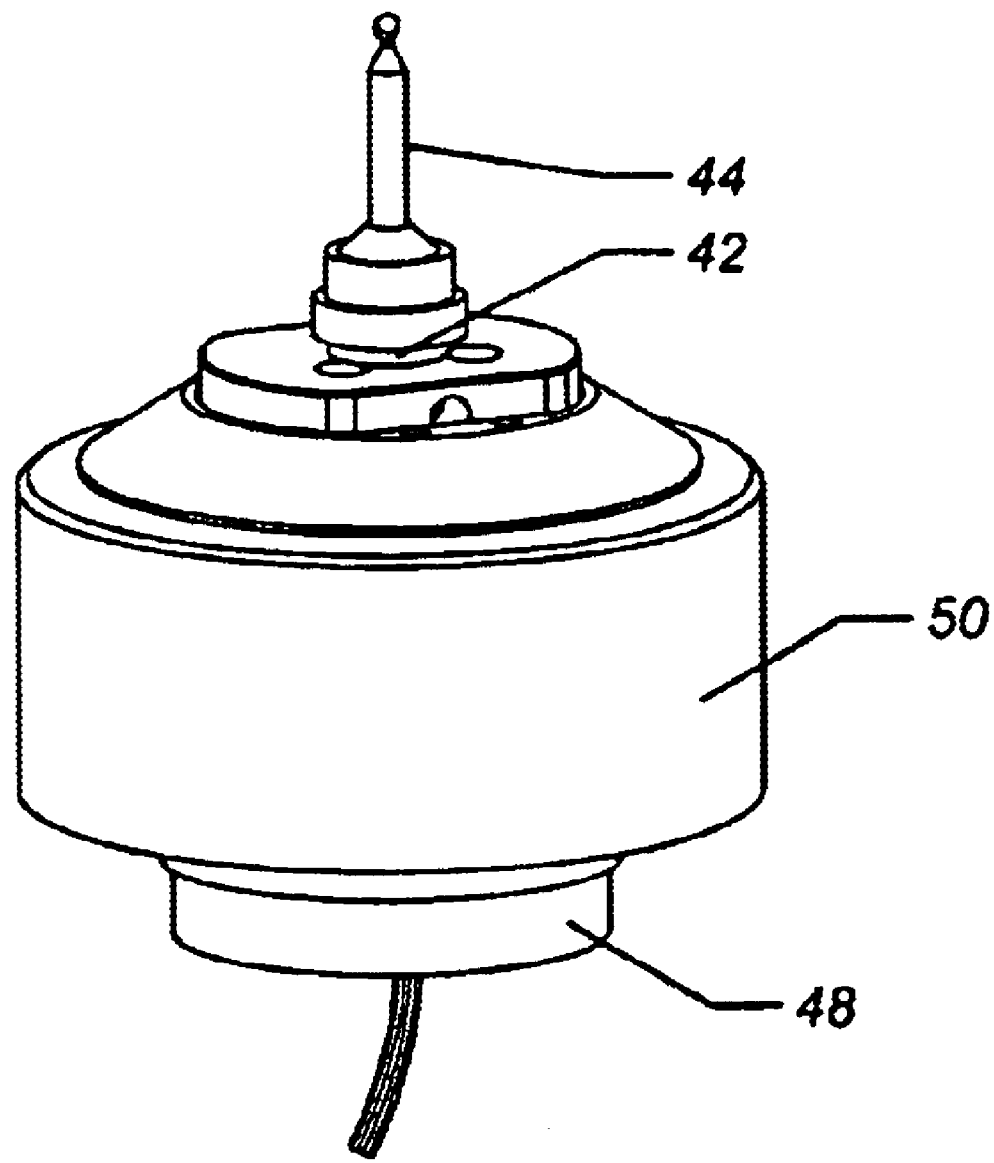
FIG. 10 is an isometric view of the fully assembled x-y-z stage micro-manipulator or positioner of the present invention.

FIG. 7 and FIG. 9 show the x-y-z-axis device 50 fully assembled. In FIG. 10, a housing may be used to protect all the working parts from the nitrogen stream used in the crystallography examination process. Similarly, as with the x-y-axis device, a magnetic base adapter 42 may be affixed to the carriage 87 of the z-axis device 80 which allows for the use of a sample-mounting pin with a ferrous base 44 to be used in conjunction with the x-y-z-axis device 50. An adapter 48 connects the device 50 to the head of a goniometer 1.

What is claimed is:

1. A micro-manipulator for a sample, especially for use at the end of a goniometer comprising:
    a y-axis device including a pair of low friction linear slides mounted in spaced apart and parallel position, a carriage carried by said slides in the y-axis and an electric motor rotating a threaded screw to provide step resolutions of said carriage for a substantial linear distance;
    an x-axis device including a pair of low friction linear slides mounted in spaced apart and parallel position, a carriage carried by said slides in the x-axis and an electric motor rotating a threaded screw to provide step resolutions of said carriage for a substantial linear distance; said x-axis carriage affixed at a right angle to said carriage of said y-axis device to provide orthogonal linear travel to said x-axis carriage; and
    a z-axis device including: a base mounted on said x-axis carriage, a pair of low friction linear slides mounted to said base, a rack and pinion mounted to said base, a carriage carried by said slides and rack, and an electric motor for driving said pinion to move said carriage vertically in the z-axis.

2. A micro-manipulator according to claim 1 wherein said x-device and y-device further includes a nut on said screw shaft that is affixed to said carriage.

3. A micro-manipulator according to claim 2 wherein said motor indirectly drives said screw shaft through a gear train.

4. A micro-manipulator according to claim 2 wherein said motor directly drives said screw shaft.

5. A micro-manipulator according to claim 1 wherein said step resolution of said x-axis and y-axis devices is about 1 micron.

6. A micro-manipulator according to claim 1 wherein said linear distance said y-axis and x-axis carriages may move is up to 6 millimeters.

7. A micro-manipulator for a crystal sample for use at the end of a goniometer comprising:
    a y-axis device for providing linear movement in the y-axis to a carriage of said device;
    a x-axis device for providing linear movement in the x-axis to a carriage of said device, said x-axis carriage affixed at a right angle to said y-axis carriage to provide orthogonal linear travel to the carriage of said x-axis device; and a z-axis device that includes: a base mounted on said x-axis carriage, a pair of low friction linear slides mounted to said base, a rack and pinion mounted to said base, a carriage carried by said slides and rack, and an electric motor for driving said pinion to move said carriage vertically in the z-axis.

8. A single axis micro-manipulator comprising;

a protective housing;

a U-shaped carriage in said housing, said carriage having a nut affixed thereto;

two linear actuators connecting said carriage to said housing;

a screw shaft mounted in said housing; and a motor in said housing for rotating said shaft and moving said carriage in step resolutions.

9. A single axis micro-manipulator according to claim 8 having a step resolution of about one micron.

10. A single axis micro-manipulator according to claim 9 wherein said two linear actuators comprise:

linear ball slides mounted on two opposite sides of said carriage and housing.

11. A single axis micro-manipulator according to claim 9 further including:

a spring mounted between the top portion of said carriage and the end of said U-shaped carriage to reduce backlash of said carriage.

12. A single axis micro-manipulator according to claim 11 further including:

a home sensor on said carriage.

* * * * *